United States Patent [19]

Gruidel et al.

[11] Patent Number: 5,739,439
[45] Date of Patent: Apr. 14, 1998

[54] VERTICAL STRATIFIED AIR/WATER SAMPLING DEVICE

[75] Inventors: James M. Gruidel; Lynn D. Alber; John J. Lainson, all of Hastings, Nebr.

[73] Assignee: Dutton-Lainson Company, Hastings, Nebr.

[21] Appl. No.: 586,197

[22] Filed: Jan. 12, 1996

Related U.S. Application Data

[63] Continuation of Ser. No. 539,734, Oct. 5, 1995, abandoned.

[51] Int. Cl.[6] .................... G01N 1/16; G01N 1/22
[52] U.S. Cl. .................. 73/864; 73/863.31; 73/864.51
[58] Field of Search ................. 73/864.51, 863.31, 73/863.52, 864.31, 864, 864.63, 864.65, 864.66, 864.67, 863.55, 863.56

[56] References Cited

U.S. PATENT DOCUMENTS

| 2,006,066 | 6/1935 | Brooks | 73/864.63 X |
|---|---|---|---|
| 3,638,500 | 2/1972 | Wetzel | 73/864.31 X |
| 3,830,480 | 8/1974 | Grant | 73/864.31 X |
| 4,061,036 | 12/1977 | Legille | 73/863.31 X |
| 4,074,577 | 2/1978 | Krug | 73/863.31 |
| 4,100,805 | 7/1978 | Cossin | 73/863.31 |
| 4,204,431 | 5/1980 | Schulz | 73/864.31 |
| 4,468,973 | 9/1984 | Iannacchione et al. | 73/864.63 X |
| 5,339,676 | 8/1994 | Johnson | 73/863.52 X |
| 5,408,892 | 4/1995 | Kawanami et al. | 73/863.56 X |
| 5,471,886 | 12/1995 | Kalindi | 73/864.63 |

FOREIGN PATENT DOCUMENTS

| 745782 | 5/1994 | Germany | 73/863.55 |
|---|---|---|---|
| 924 | 1/1976 | Japan | 73/864.51 |

*Primary Examiner*—Thomas P. Noland
*Attorney, Agent, or Firm*—Banner & Witcoff, Ltd.

[57] ABSTRACT

An application disclosed for collecting a plurality of gas or liquid samples at a plurality of vertical heights above a surface. The apparatus comprises a vertical support member, a sample support rod connected to the vertical support and moveable between a vertical position and a horizontal position, and one or more sample receivers, freely and pivotally suspended from the sample support rod from points along the rod, for trapping airborne material. The sample receivers maintain vertical orientation as the sample support rod is pivoted from a vertical to a horizontal position during collection of the samples.

12 Claims, 4 Drawing Sheets

VERTICAL STRATIFIED AIR/WATER SAMPLING DEVICE

This is a continuation of application Ser. No. 08/539,734, filed Oct. 5, 1995 and now abandoned.

BACKGROUND OF THE INVENTION

1. Field of the Invention

This invention relates generally to an apparatus for collecting a plurality of gas or liquid samples at a plurality of vertical heights above a surface.

2. Background of the Invention

In many circumstances, it is desirable to collect samples of airborne gases or liquids at various levels above a ground surface. One notable example is in the case of a newly developed method for removing volatile contaminants from water, in which the contaminated water is sprayed through a central pivot sprinkler system, with the volatile contaminants evaporating from the water as it passes through the atmosphere. In that situation, samples of the cleaned water are taken at various heights or stages of solvent evaporation to determine the efficiency of the cleaning process.

Known prior art methods for collecting such samples have suffered several drawbacks. Most notably, the prior art has not provided sample collection systems that are easy to use, and which allow collection of samples at a plurality of different heights and from a plurality of different directions, while allowing easy retrieval of the samples after they have been collected.

It is thus an object of the present invention to provide an apparatus that is capable of collecting air or water samples at a plurality of different heights above a ground surface, and from a plurality of different directions.

It is also an object of the present invention to provide a sample collection device that allows the samples to be easily retrieved by a technician or researcher, without having to disassemble the sample collection system or reach upwards toward the higher-located samples.

It is also an object of the present invention to provide a sample collection apparatus that is simple in construction, and easy to assemble and disassemble at a given test site.

It is also an object of the present invention to provide a sample collection apparatus that will allow a plurality of samples to be retrieved from various heights, without disturbing or spilling the samples.

These, and many other objects, advantages and features of the invention are set forth in the detailed description which follows.

SUMMARY OF THE INVENTION

In a basic aspect, the invention is an apparatus for collecting a plurality of gas or liquid samples at a plurality of vertical heights above a surface. The apparatus comprises a vertical support, a sample support rod that is pivotally connected to the vertical support, and one or more sample receivers that are connected to the sample support rod from attachment points along the rod. Samples are collected in the sample receivers, and the sample support rod is then pivoted downward from a vertical position to a horizontal position, to allow easy collection of the samples. In a preferred embodiment, the sample receivers are freely and pivotally suspended from the sample support rod, and are thus free to maintain a vertical orientation as the sample support rod is pivoted from a vertical to a horizontal position during retrieval of the samples. The sample receivers can also be pointed in a variety of different direction, to allow collection of multiple samples from different directions and heights.

The apparatus is lightweight, inexpensive, and easy to assemble and operate. In addition, the apparatus provides a consistent and dependable means for collecting samples, and allows samples taken from substantial heights to be retrieved without spillage, and without climbing.

DETAILED DESCRIPTION OF THE PREFERRED EMBODIMENTS

Figure 1:
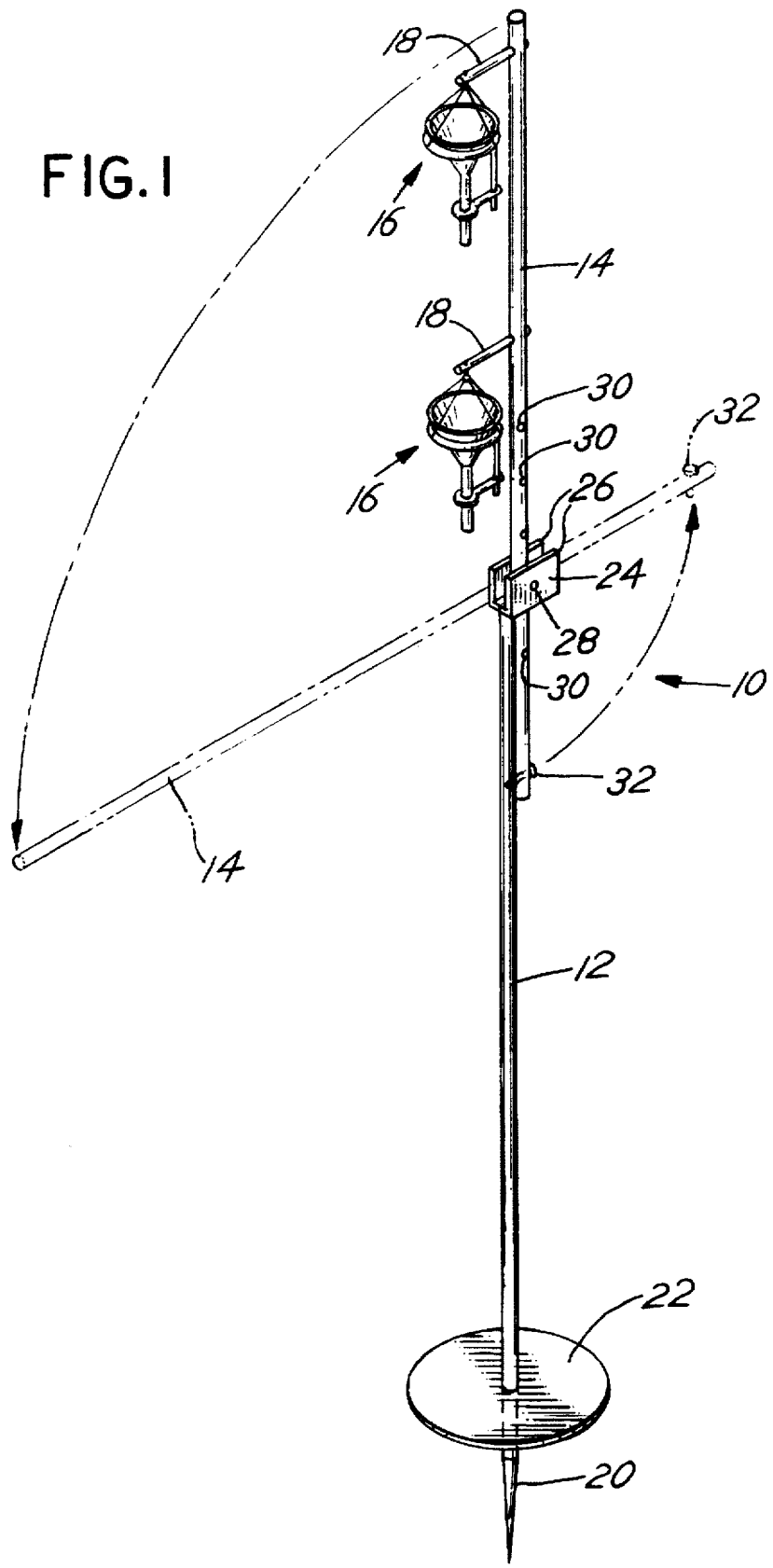
FIG. 1 of the drawing is an isometric view of the apparatus in accordance with one embodiment of the present invention.

Referring to FIG. 1 of the drawing, a preferred embodiment of the invention is shown. The apparatus 10 includes a vertical support member 12, a sample support rod 14 pivotally attached to the vertical support member 12, and a plurality of sample receivers 16 connected to the sample support rod 14 at spaced points along the rod. The member 12 is typically ten (10) to twenty (20) feet long and may be supported in the earth by guy wires or support legs (not shown). The lower end 20 of the vertical support 12 is preferably pointed, allowing that end 20 of the apparatus to be easily forced into the ground to support the apparatus in an overall vertical orientation. A base plate 22 is provided, to stabilize the apparatus laterally, and to control the depth of the member 12 within the ground.

The vertical support member 12 and the sample support rod 14 typically comprise metal rods or tubes, which may be a single uniform rod or may be a series of telescoping members. However, it will be understood to persons of skill in the art that a variety of alternate structures can be used for these components. By way of example, either the vertical support member 12 or the sample support rod 14 can be an A-frame, an I-beam, or other such structure. The relative dimensions of the vertical support member 12 and the sample support rod 14 can also be varied, depending on the particular circumstance under which the apparatus is to be used. In addition, while the vertical support and the sample support rod are preferably made of tubular aluminum or stainless steel, they can also be composed of wood, plastic or other such materials.

The sample support rod 14 is pivotally connected to the vertical support member 12 by means of a pivot or hinge mechanism 24 attached to the vertical support member 12. The hinge mechanism 24 comprises opposed parallel, spaced plates 26, attached to the top of support member 12, and between which the sample support rod 14 is positioned. A hinge pin 28 passes through aligned horizontal openings in the opposed plates and through a passage or hole 30 in the sample support rod 14. A plurality of holes 30 are provided along the length of the sample support rod 14, whereby the height of the support rod 14 can be adjusted by moving an appropriate hole 30 into alignment with the hinge pin 28.

Means are also provided for securing the sample support rod 14 in a desired position relative to the vertical support member 12. While the particular means shown in FIG. 1 is a bolt 32 that passes through the sample support rod 14 and threads into the vertical support member 12, it will be understood to persons of ordinary skill that a number of different means can be provided for accomplishing this function. For instance, the means can include a strap or clamp (not shown) that passes around the vertical support member 12 and the sample support rod 14. The means can also include a clamp, pin or friction plate (not shown) associated with the hinge assembly 24.

Figure 2:
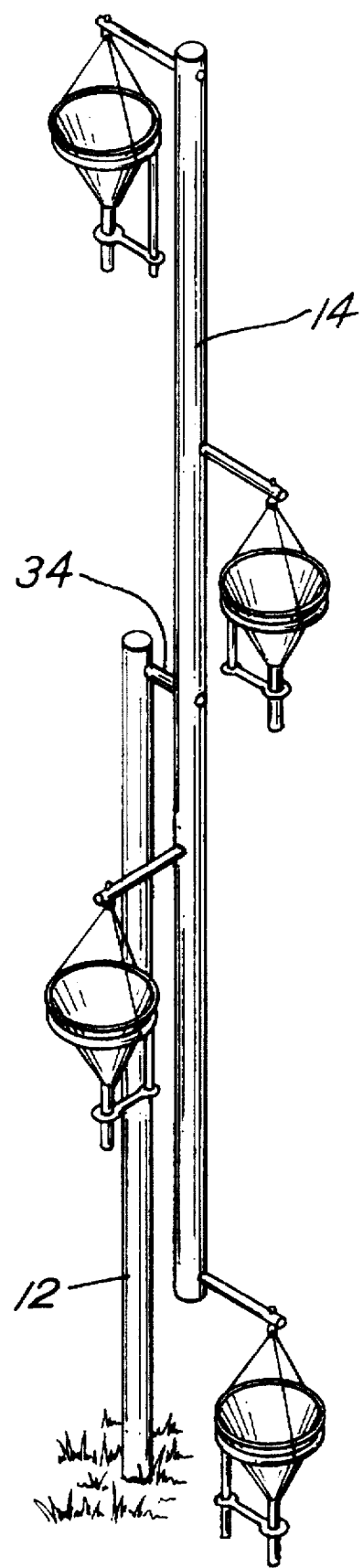
FIG. 2 of the drawing is an isometric view of the apparatus in accordance with another embodiment of the present invention.

Similarly, a number of different approaches can be used for hinging the sample support rod 14 from the vertical support member 12. For instance, as shown in FIG. 2, the hinge assembly 24 can comprise a pivot shaft or arm 34 that extends in a perpendicular direction from the vertical support member 12. The sample support rod 14 is then pivotally attached to the end of the pivot shaft 34.

Turning to the sample receiver 16, the purpose of the sample receiver 16 is to trap or collect the material being sampled, and to direct the material into a sample container of some sort. While it is generally envisioned that a plurality of sample receivers 16 will be used on each apparatus 10, to allow a plurality of samples to be collected at one time, the apparatus can be operated with only a single sample receiver 16, if so desired.

Figure 3:
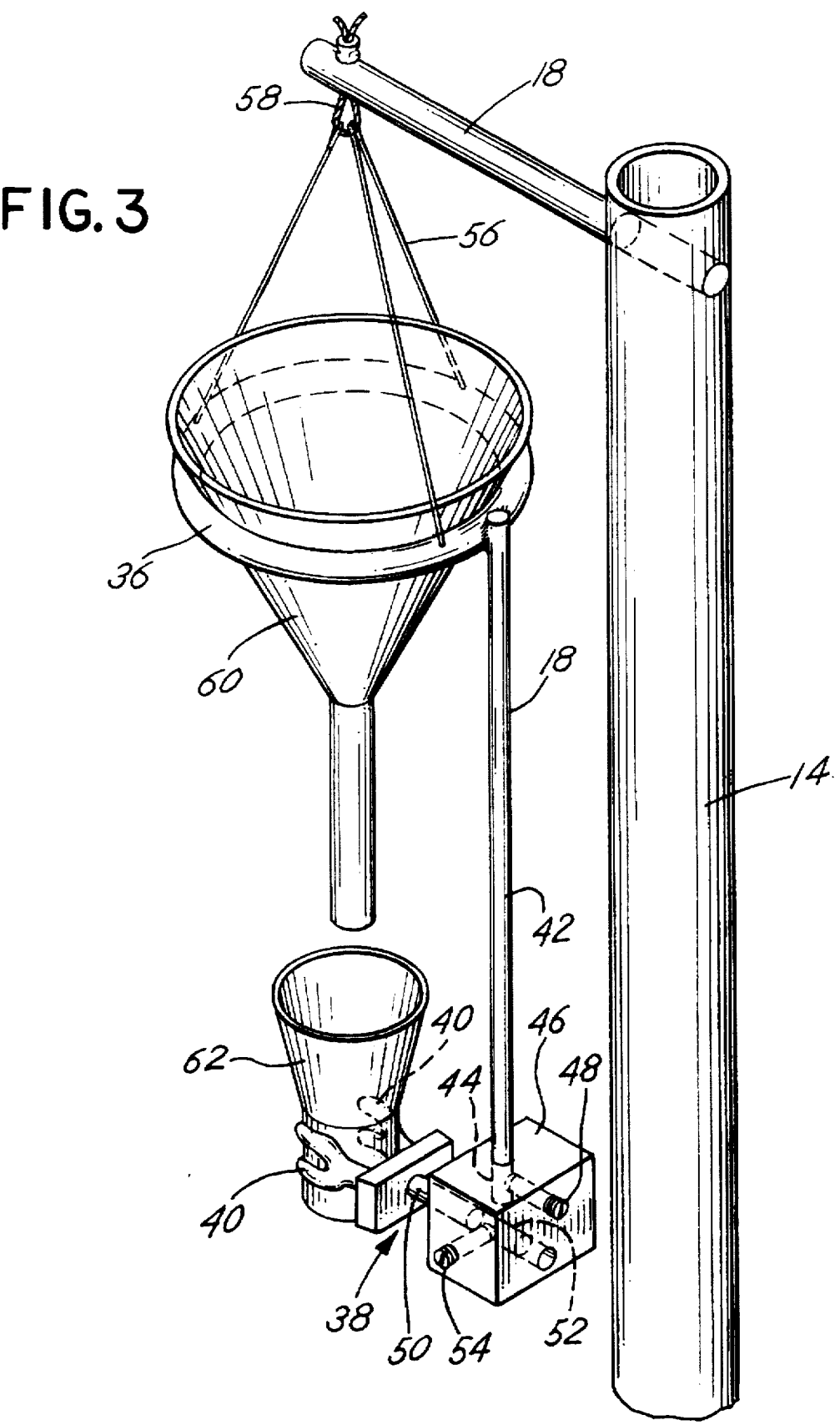
FIG. 3 of the drawing is an enlarged isometric view depicting the details of a preferred sample receiver used in combination with the assembly comprising the invention.

Details of a particularly preferred embodiment of the sample receiver 15 are shown in FIG. 3. As shown in that Figure, the sample receiver generally comprises a funnel 60 in combination with a sample container 62. The funnel 60 and the sample container 62 are positioned within a funnel support 18, which comprises a ring 36, made of one-quarter inch (¼") stainless steel, and a container clamp 38 with adjustable tongs 40 for gripping a container. The ring 36 and the sample clamp 38 are connected to one another by a quarter inch (¼") stainless steel rod 42. One end of the rod 42 is connected to the outer perimeter of the ring 36, perpendicular to the ring, and the other end of the rod 42 fits into a bore 44 drilled into an aluminum block 46. A set screw 48 or other such means is provided in the aluminum block 46 for securing the rod 42 in position within the block. Similarly, a longitudinal support extension 50 of the container clamp 38 passes into a second bore 52 drilled into the aluminum block 46, and is secured by a second set screw 54 or other securing device. By loosening the set screws 48 and 54, the relative position of the ring 36 and the container clamp 38 can be adjusted to a variety of positions, to accommodate different size funnels and sample containers.

In operation, a funnel 60 is placed onto the ring 36 of each sample holder 16, and a sample container 62 is placed into the sample container clamp 38, beneath the funnel 60. This arrangement allows the funnel and/or the sample container to be easily replaced and cleaned after each test run, to avoid contamination in subsequent tests. In addition, one funnel 60 can easily be replaced by a different size funnel 60, to vary or adjust the rate at which samples are collected, or to otherwise standardize the sampling operations in a desired manner.

As shown in FIG. 3, each sample receiver 16 is freely and pivotally suspended from an arm 18 by nylon strings 56, which are connected to the arm 18 at a single point in a known manner, such as by a cable, wire loop or hook 58. Each sample receiver 16, being freely and pivotally suspended from the sample support rod 14, is free to maintain a constant orientation as the sample support rod 14 is pivoted from a vertical to a horizontal position during retrieval of the samples. This allows the sample receiver 16 and the sample container 62 to be accessed by a technician without the danger of spilling the sample contained within the sample container 62.

The embodiment shown in FIG. 3 can be modified in many different ways. By way of example, the funnel 60 can be suspended directly from the arm 18 or the support arm 14, via strings 56, without using the funnel holder 18. The sample container 62 can also be integrated into the funnel 60, or can be suspended directly from the funnel.

Figure 4:
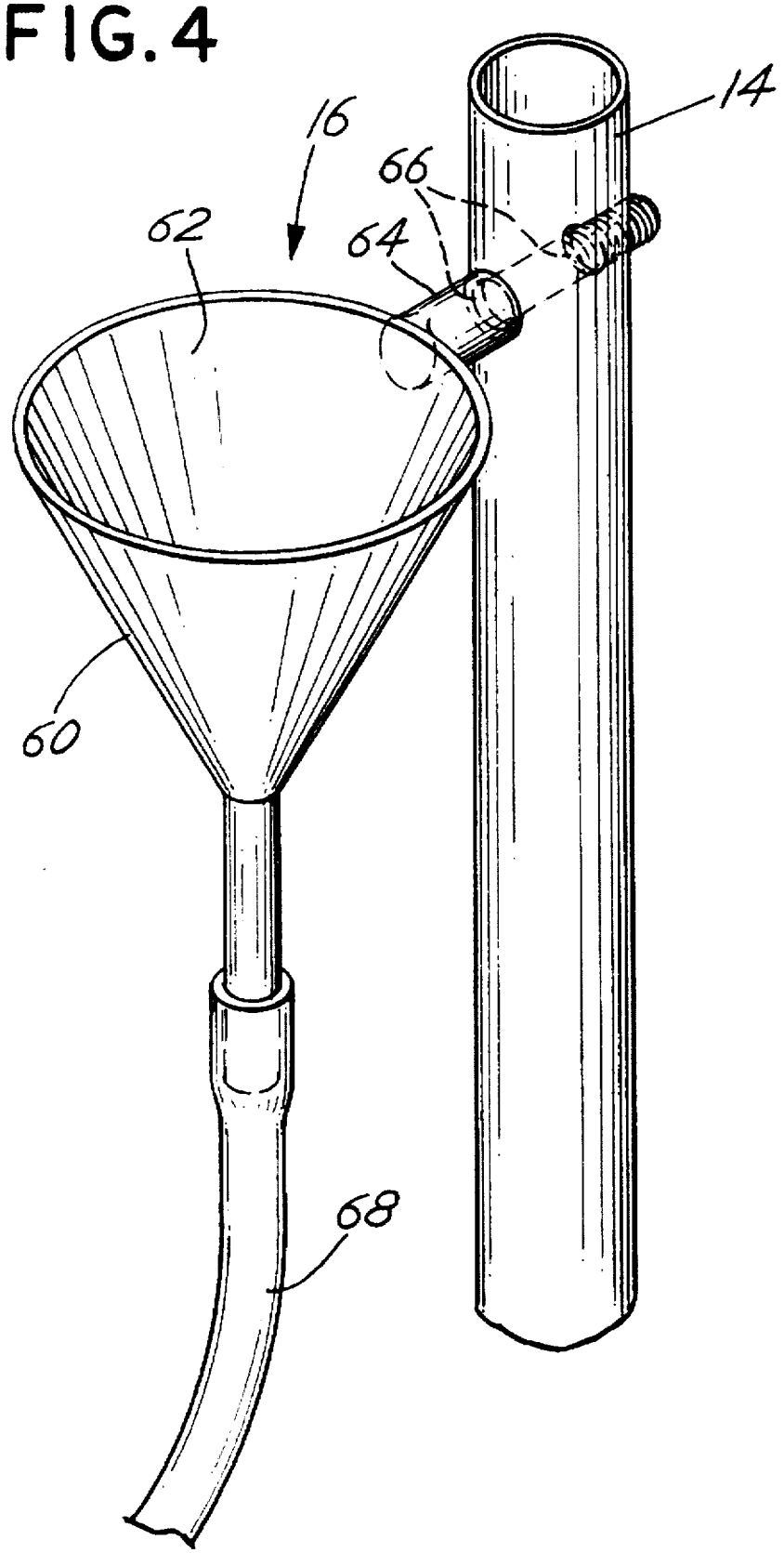
FIG. 4 of the drawing is an enlarged isometric view depicting the details of another preferred sample receiver used in combination with the assembly comprising the invention.

Another embodiment of the sample receiver 16 is shown in FIG. 4. In that embodiment, the sample receiver 16 comprises a funnel 60, which remains fixed in position with respect to the sample support arm 14 during movement of the support arm. The funnel 60 includes a threaded longitudinal extension (24, which passes through a bore 66 in the sample support arm 14. A nut or other fastener (not shown) is threaded onto the end of the extension 64 to secure the funnel 60 in place. A flexible tube 68 leads from the funnel 60 to a remote sample container (not shown).

In most circumstances, the sample receiver will be oriented vertically during sample collection, with the mouth of the sample receiver 16 or funnel 60 pointing upwards. However, in some situations, such as when collecting airborne materials that are moving horizontally, it may be desirable to tip the sample receiver so that the mouth of the sample receiver 16 or funnel 60 is pointing in a non-vertical direction. In the embodiment shown in FIG. 4, that is accomplished by loosening the nut from the extension (64, and rotating the sample holder 16 to a desired non-vertical position. Each sample receiver 16 can be oriented in a different direction, to allow simultaneous collection of airborne samples from different directions, at a variety of different heights.

The above described embodiments allow collection of samples at a number of different vertical or horizontal points. Moreover, each individual sample receiver can be oriented in a different desired direction, to allow simultaneous collection of different samples from different directions, at different heights. In addition, the apparatus allows samples to be retrieved by a technician or researcher without disturbing the samples or spilling the samples from the collection containers.

While in the foregoing specification there have been described various preferred embodiments of the invention, it should be understood to those skilled in the art that various modifications and changes can be made to those preferred embodiments without departing from the true spirit and scope of the invention as recited in the claims.

What is claimed is:

1. An apparatus for collecting a plurality of samples at a plurality of vertical heights above a surface, said apparatus comprising, in combination;
   a) a vertical support member;
   b) a sample support rod, connected to the vertical support and moveable between a vertical position and a horizontal position; and
   c) a plurality of sample receivers connected to the sample support rod at points along the rod.

2. The apparatus of claim 1 wherein at least some of the sample receivers are freely and pivotally suspended from the sample support rod, whereby the freely and pivotally suspended sample receivers maintain a constant vertical orientation as the sample support rod is pivoted between the vertical and horizontal position.

3. The apparatus of claim 1, wherein the sample support rod is pivotally connected to the vertical support member by a hinge mechanism.

4. The apparatus of claim 3, wherein the hinge mechanism comprises first and second opposed plates, spaced apart from one another on opposite sides of the sample support rod, and a hinge pin that passes through the first and second plates and the sample support rod.

5. The apparatus of claim 4, wherein the hinge mechanism comprises a pivot shaft that extends perpendicularly from the vertical support member and through the sample support rod, whereby the sample support rod pivots axially about the shaft.

6. The apparatus of claim 1 wherein the sample support rod comprises a plurality of spaced arms extending outward from the sample support rod, at least one sample receiver being suspended from each arm.

7. The apparatus of claim 1 including means for securing the sample support in a fixed position relative to the vertical support member.

8. The apparatus of claim 7, wherein the means for securing the sample support rod in a fixed position comprises a bolt that passes through the sample support rod and threads into the vertical support member.

9. The apparatus of claim 1, wherein each sample receiver comprises a funnel in combination with a sample container.

10. The apparatus of claim 9, further comprising a funnel support for supporting the funnel and the container in a position relative to one another, said funnel support comprising a ring, a container clamp and a two ended rod, one end of the two ended rod being connected to the ring and the other end of the two ended rod being connected to the container clamp, the ring being adapted to receive the funnel and the container clamp being adapted to receive the sample container.

11. The apparatus of claim 1, wherein the vertical support member and the sample support rod are made of rigid tubular material.

12. An apparatus for collecting a sample at a desired vertical height above a surface, said apparatus comprising, in combination:

a) a vertical support member, b) a sample support rod, connected to the vertical support member and moveable between a vertical position and a horizontal position, c) a sample holder freely and pivotally suspended from the sample support rod, whereby the sample holder maintains a vertical orientation as the sample support rod is pivoted between the vertical and horizontal position.

* * * * *